(12) United States Patent
Hoering et al.

(10) Patent No.: US 8,511,175 B2
(45) Date of Patent: Aug. 20, 2013

(54) SENSOR ELEMENT

(75) Inventors: Gert Hoering, Karlsruhe (DE); Jafar Zendehroud, Kassel (DE)

(73) Assignee: AMG Intellifast GmbH, Speyer (DE)

( * ) Notice: Subject to any disclaimer, the term of this patent is extended or adjusted under 35 U.S.C. 154(b) by 233 days.

(21) Appl. No.: 12/976,828

(22) Filed: Dec. 22, 2010

(65) Prior Publication Data

US 2011/0146412 A1    Jun. 23, 2011

(30) Foreign Application Priority Data

Dec. 22, 2009    (DE) .................. 10 2009 060 441

(51) Int. Cl.
*G01L 1/00* (2006.01)
(52) U.S. Cl.
USPC .......................................................... 73/776
(58) Field of Classification Search
USPC ........... 73/776, 774, 767; 29/25.35; 310/338
See application file for complete search history.

(56) References Cited

U.S. PATENT DOCUMENTS

| | | | |
|---|---|---|---|
| 5,153,859 A * | 10/1992 | Chatigny et al. | 367/140 |
| 7,248,133 B2 * | 7/2007 | Koga et al. | 333/193 |
| 2008/0129150 A1 * | 6/2008 | Zhang | 310/329 |
| 2011/0109200 A1 * | 5/2011 | Jenninger et al. | 310/338 |

FOREIGN PATENT DOCUMENTS

| | | |
|---|---|---|
| DE | 42 24 035 A1 | 1/1994 |
| DE | 42 32 254 A1 | 4/1994 |
| DE | 10 2004 038 638 | 6/2006 |

* cited by examiner

*Primary Examiner* — Jewel V Thompson
(74) *Attorney, Agent, or Firm* — Muncy, Geissler, Olds & Lowe, PLLC

(57) ABSTRACT

A connection component is provided that includes an integrated ultrasound sensor, wherein the ultrasound sensor has a layer structure comprising at least two layers, with an electrode layer and at least one layer of a material having piezoelectric properties. The at least one electrode layer and the at least one layer of a material having piezoelectric properties are arranged on a freely accessible end of the connection component. Structures are formed in the electrode layer in order to produce electrodes by laser-ablated regions.

18 Claims, 6 Drawing Sheets

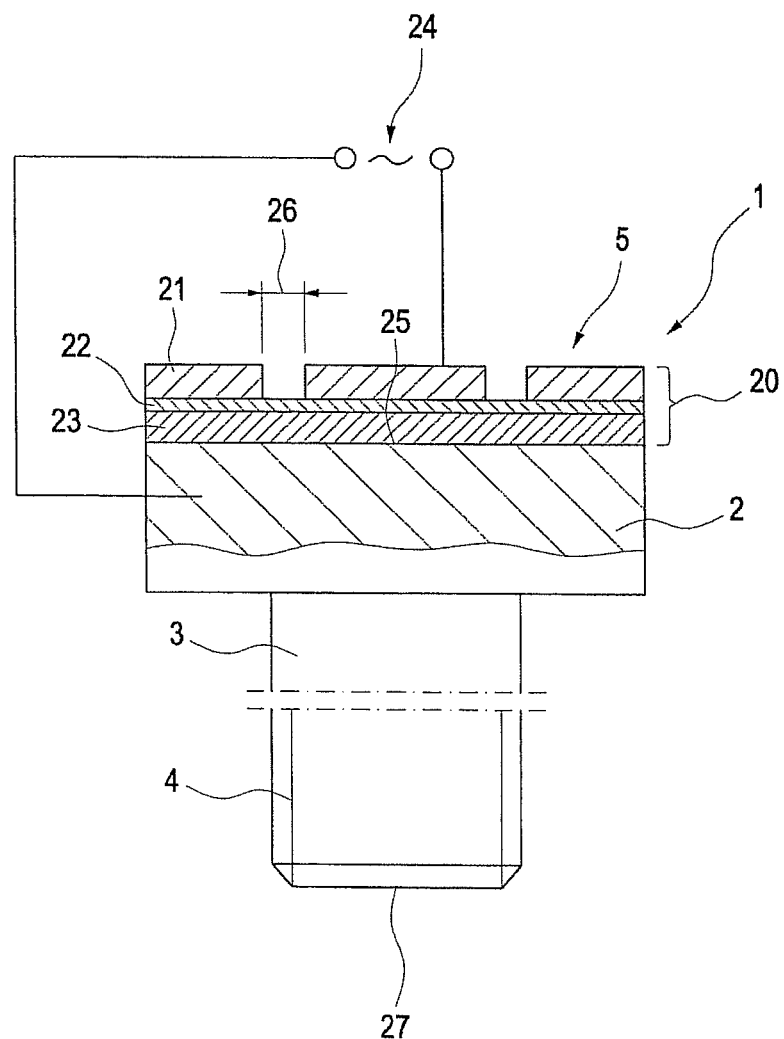
Fig. 2.1

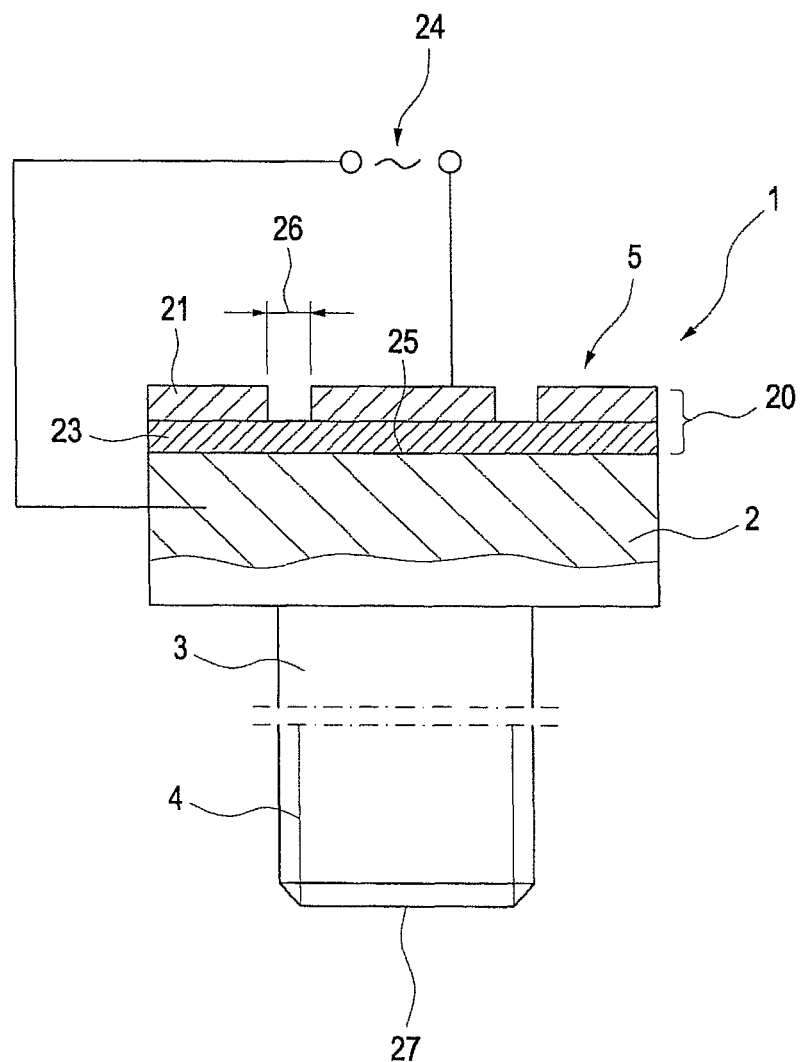
Fig. 2.2

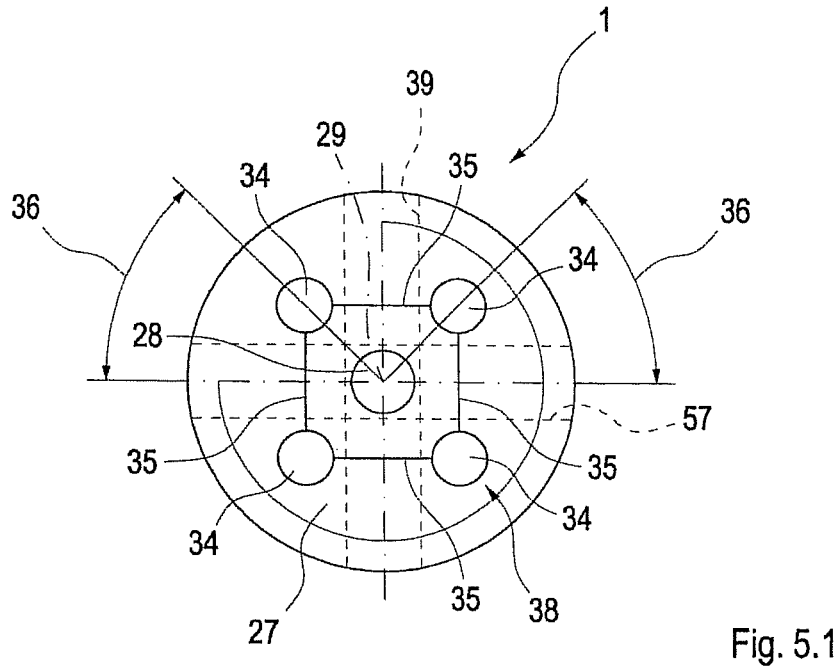
Fig. 5.1
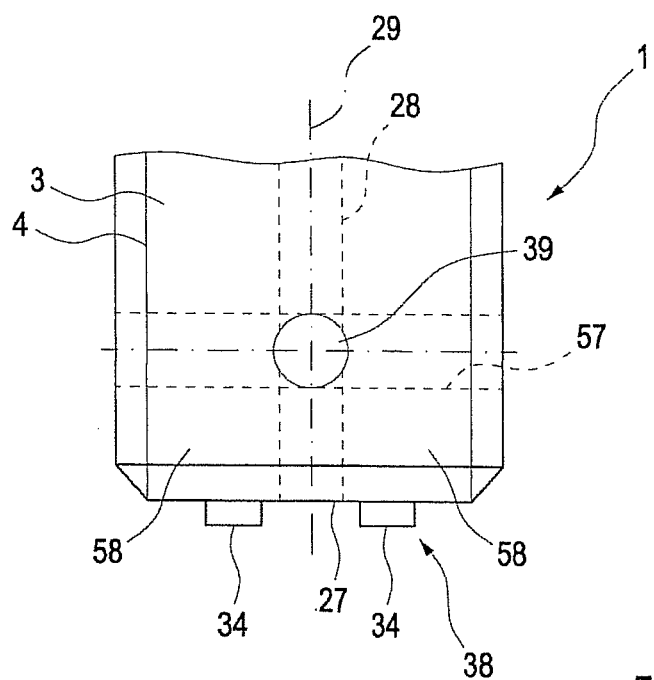
Fig. 5.2

SENSOR ELEMENT

This nonprovisional application claims priority under 35 U.S.C. §119(a) to German Patent Application No. DE 10 2009 060441.3, which was filed in Germany on Dec. 22, 2009, and which is herein incorporated by reference.

BACKGROUND OF THE INVENTION

1. Field of the Invention

The present invention relates to a connection component having an integrated ultrasound sensor, wherein the ultrasound sensor has a layer structure having at least two layers, with an electrode layer and at least one layer of a material having piezoelectric properties.

2. Description of the Background Art

Ultrasound testing methods are known from DE 42 24 035 A1 and DE 42 32 254 A1.

DE 10 2004 038 638 relates to a connection component, in the head region of which there is an ultrasound sensor whose structure is formed as a layer structure.

Nowadays, for example, adhesively bonded sensors comprising PVDF films or adhesively bonded sensors made of ceramic material are employed as ultrasound transducers, which are also referred to as ultrasound sensors. Ultrasound sensors made with PVDF films are highly sensitive and are applied, for example, onto screw heads of connection components formed as screws. Application and fixing on a screw head are generally carried out by means of an adhesive layer. PVDF films have the disadvantage that they are not thermally stable. Beyond a temperature of about 70° C. an ageing process takes place in the PVDF film, which in the extreme case can lead to disintegration of the PVDF film. The basic problem with PVDF films is separation of the film over the operating time, or partial separation of the film material, owing to weakening of the bonding force of the adhesive. If the prestress force or the stress force of a connection component configured in the form of a screw is then measured with the aid of an ultrasound sensor, which is made of PVDF film or piezoceramic, then the partial separations which for example occur owing to high thermal loads below the sensor are not visible. Owing to the partial separations and the unknown local position of the partial separations, a false measurement result is obtained by an ultrasound measurement with such a predamaged ultrasound sensor, since the signal propagation times are vitiated owing to the ultrasound signal path length being lengthened by the partial separations. In the event of full separation of the PVDF film or the piezoceramic, in the extreme case an ultrasound measurement is no longer possible at all. The vitiations which occur can lead to considerable errors which can vitiate a result based on a time of flight measurement of an ultrasound signal, or even make it entirely unusable.

It is furthermore known to use a coupling gel in ultrasound measurements, although this is unsuitable for determining a prestress force in a connection component in the form of a screw, since even very small differences when positioning the test head cause ultrasound coupling input time differences which can be greater than the measurement value itself. The required accuracy classes cannot generally be achieved by ultrasound measurements in which a coupling gel is used.

In a vapour deposition method for producing ultrasound sensors, three steps are generally carried out. First, a piezo layer is sputtered onto the cleaned connection elements, generally formed as screws, on one of the two ends. Instead of screws, other connection elements may also be provided with a piezo layer by means of the vapour deposition method, for example rivets or bolts or the like. In a second coating step, a protective layer is applied which is intended to protect the piezo layer against environmental effects. The protective layer is not, however, categorically necessary. Before a further layer can be vapour deposited, namely a metallization layer for the electrodes of the sensors, the connection components are masked. This is necessary in order to be able to produce the electrodes required for the electrical excitation of the sensors. Only by masking is a functional ultrasound sensor obtained from the above-described two- or three-layered system comprising a piezo layer, optionally a protective layer, and a metallization layer. When suitable materials are used, in particular thermally stable and environmentally resistant piezo materials, application of the protective layer can be obviated so that a two-layered system is obtained instead of the three-layered system.

Currently, masking of the plane sides of the connection components is carried out manually by using self-adhesive polyimide film or stamped magnetic masks, although the latter only adhere to components which have ferromagnetic properties. The time outlay, and the concomitant financial expenditure, for manually performed masking of the connection components are considerable. Also, the masking currently carried out manually always entails the risk that the ends of the connection components, for example screws, may be partially contaminated before the vapour deposition of the electrode, which can lead to bonding problems of the metallization layer. Furthermore, the above-described masking method is restricted to simple structures, for example annular structures. As soon as more complex structures are to be made, the manual masking method reaches its limitations.

SUMMARY OF THE INVENTION

It is therefore an object of the present invention to provide a connection component comprising an integrated ultrasound sensor in an automated or semiautomated fashion.

According to an embodiment of the invention, a structure for forming at least one electrode is produced by laser ablation after having carried out surface-wide coating of a side, for example configured as a plane surface, of a connection component, for example a screw, a bolt, a rivet or the like, with a piezoelectric thin film, a protective layer and an electrode layer. Instead of forming one side of a connection component as a plane side, it is also possible to configured it convexly or concavely curved, which will depend on the application. In the present context, the connection component is for example a component made from a metallic material or one made from an alloy of metallic materials. In this case, the mass of the component constitutes one electrode. On this metal component, at least one electrode is formed in accordance with the method proposed according to the invention. The solution proposed according to the invention may, however, also be implemented on connection components which have a nonmetallic material, for example a ceramic, which is electrically nonconductive. The connection component is to be provided with a metallization in order to produce the component mass in an additional first coating step, followed by at least one layer having piezoelectric properties, a protective layer and at least one further metallization. According to the invention, the at least one electrode is also produced on electrically nonconductive connection components by lasering. In the present context, for the sake of completeness, it is also to be pointed out that the connection components, whether made of metallic material, nonmetallic material or an electrically nonconductive material, may be components which have a self-tapping screw thread that is formed on the outside of the connection component, in particular a connection component in the form of a screw.

Lasering represents a tried and tested method nowadays. Lasering makes it possible to produce electrodes with an arbitrarily complex structure, which are insulated from one another. Laser ablation of an arbitrary structure, for example a circle as a circular electrode surface on the one hand, and the screw material as the back electrode on the other hand, makes it possible to obtain the ultrasound sensor. One electrode is constituted by the laser-ablated surface, for example formed as a circular surface, while the back electrode is constituted by the material of the connection component. Whereas only simple structures can be produced by the manual masking method outlined above in connection with the prior art, structures having much more complex geometries can be fabricated by laser ablation, even entire sensor arrays, which cannot be produced by the manual masking method. In particular, by laser ablation of the at least one electrode in order to produce the ultrasound sensor, the latter can be adapted to the structure of the component, for example to the geometry of a screw or bolt or rivet head. A very wide variety of connection elements, for example screws, bolts, rivets or tie-rods or the like, can be provided with at least one ultrasound sensor on one of the end sides. Instead of one ultrasound sensor on the end sides, groups of sensors or entire sensor arrays can also be produced by means of the laser ablation of electrodes. It is thus in particular very readily possible to adapt the sensor structure, i.e. its geometry, optimally to the connection element. By laser ablation of electrode structures with a complex geometry, ultrasound sensors can be applied onto connection elements having longitudinal or transverse bores, for example screws or hollow bolts. In the case of components having a longitudinal bore, which are primarily stressed by shearing, a ring electrode, which is arranged around the bore, is made from an electrode originally having a circular appearance, which is used for example for connection elements without a through-bore. An adapted sensor structure can furthermore be made, for example for connection elements which have two transverse bores crossing in the direction of the axes. In this case, by the laser ablation of the electrodes as proposed according to the invention, it is possible to ensure that the ultrasound sensors are not arranged above intersecting bores in the material of the connection component, but instead where the propagation of the ultrasound signal is not hindered by the transverse bores so that the applied ultrasound pulse delivers a meaningful and evaluable echo signal.

By such a degree of freedom in the positioning of the ultrasound sensors, the propagation path of the ultrasound pulse can be configured optimally so that an evaluable ultrasound echo signal is obtained. If the ultrasound sensors, in this case for example four ultrasound sensors, are applied on the end side of the component to be measured so that the transverse bores interfere only slightly with the propagation path of the ultrasound signal, then an evaluable echo signal can be obtained. In this case, the four individual ultrasound sensors are electrically coupled to one another so as to obtain a composite sensor which comprises four individual ultrasound sensors.

In continuation of this concept, an ultrasound sensor comprising complex sensor structures can be obtained from such a composite sensor. A plurality of sensor elements may in this case be arranged in a matrix fashion. The individual elements of the matricially arranged ultrasound sensors may be driven individually, or alternatively interconnected to form groups of different size within various preselectable sets.

The laser ablation of the electrode layer, i.e. the production of a sensor structure therein, avoids an electrical short circuit between the electrodes which are separated from one another by the laser-ablated surfaces.

A protective layer lying below the metallization layer in the layer structure is not fully penetrated by the laser radiation; instead, it is merely eroded superficially.

Electrodes produced by means of automated laser ablation in the electrode layer of the layer structure of a connection component comply with the previously demanded requirements for the stability of the sensors in relation to a salt spray test.

When laser-ablating the at least one electrode with a complex and arbitrary geometry, after erosion of the top cover layer it is necessary to ensure that the underlying layers are not damaged. The erosion behaviour when lasering depends on the absorption capacity of the metallization and of the underlying protective layer. By suitable selection of the laser wavelength and other parameters for the lasering, it is possible to accommodate particular layer properties, for example the absorption capacity. According to the invention, the laser ablation of the electrodes is carried out so that, when laser-ablating surfaces which are closed on themselves, the laser beam produces only one entry point without having to be reapplied again. The structure to be produced along a displacement path is made in one working step. This can advantageously achieve the effect that a briefly elevated energy input at the entry points of the laser beam occurs only once. When laser-ablating by means of the method proposed according to the invention, it is possible to avoid damage to an optionally provided protective layer, which covers the piezo layer and which may be part of a three-layered structure of the ultrasound sensor.

If, following the method proposed according to the invention, a structure which produces electrodes with a different complex geometry is made, then an additional electrode may be laser-ablated in a further working step on an end side of the connection component, on which the ultrasound sensor is intended to be produced by laser ablation. This electrode constitutes a reference electrode. By virtue of this additional electrode, which may optionally be produced simultaneously, a temperature measurement may for example be carried out. This electrode can lie in a region of the component which does not experience mechanical stresses that could vitiate the measurement result. To mention the example of screw heads, the end side of the screws outside the perpendicular projection surface of the screw shank is suitable for this.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
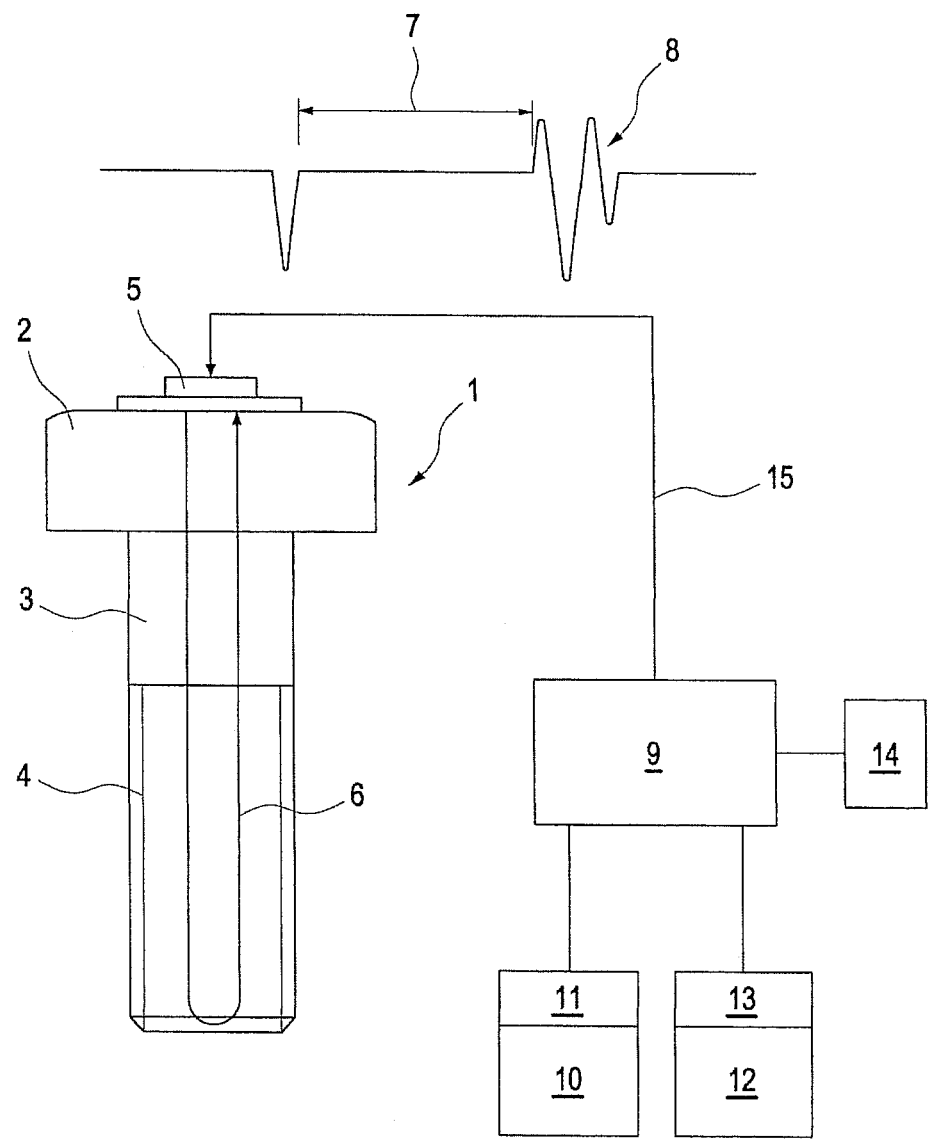
FIG. 1 shows a device for carrying out an ultrasound measurement of a connection component formed as a screw, FIG. 2.1 shows a section represented on an enlarged scale through a structure, formed in three layers, of the ultrasound sensor formed on the upper side of the connection component, FIG. 2.2 shows a section represented on an enlarged scale through a layer structure, formed in two layers, of the ultrasound sensor formed on the upper side of the connection component.

The representation according to FIG. 1 shows a connection component, which is formed as a screw. The connection component may furthermore be configured as a connection bolt comprising an external screw thread formed on one side or on both ends, or the like.

The connection component 1 represented in FIG. 1 comprises a screw head 2 and a shank 3. A threaded part 4 which can be screwed into a screw thread, complementary to it, of a component or provided with a screw nut, extends below the shank 3. Above the screw head 2, there is an ultrasound sensor 5 for an ultrasound pulse 7 to be input into the connection component 1. The ultrasound pulse 7 input into the connection component 1 at the ultrasound sensor 5 travels along a propagation path 6 through the connection component 1 and emerges again from the connection component 1 at the ultrasound sensor 5 as an electrical ultrasound pulse echo 8. The time which elapses between the entry of the ultrasound pulse 7 into the connection component 1 and the emergence of the ultrasound pulse echo 8 from the connection component 1, i.e. the time of flight of the ultrasound signal, is denoted by t.

For input of the ultrasound pulse 7 into the connection component 1 and extraction of the electrical ultrasound echo 8 therefrom, a signal transmission line 15 which may be formed as a coaxial cable, having an impedance characteristic of the signal transmission line 15, extends between the ultrasound sensor 5 and an ultrasound measuring instrument 9. The ultrasound measuring instrument 9 is connected to a computer 14, which may for example be a PC. The ultrasound measuring instrument 9 is furthermore connected to a pulse generator 10 (arbitrary function generator) to which a first power amplifier 11 may be allocated. By means of the pulse generator 10 with the first power amplifier 11, the ultrasound pulses 7 are generated with the interposition of the ultrasound sensor 5. A transient recorder 12, which may comprise a signal amplifier 13, is used for signal acquisition of electrical ultrasound pulse echoes 8 extracted from the connection component 1. In order to determine the propagation time existing at the time of measuring the stress force in the signal transmission line 15, and the propagation times of the ultrasound signal through the electronic measuring instrument 9, reflection of an electrical excitation signal at the end (at the ultrasound sensor 5) of the signal transmission line 15 is used.

The representation according to FIG. 2.1 shows the connection component without evaluation peripherals but with an integrated ultrasound sensor element, on an enlarged scale.

The connection component 1 represented in FIG. 2.1 can be, for example, configured as a screw. Besides this, the connection component 1 may also be formed as a bolt, a pin or a rivet or the like. The connection component 1 comprises at one or both ends a shank-shaped section 3 on which a screw thread 4 is formed. On a first end 25, which constitutes the end side of a screw head 2, the ultrasound sensor 5 which is formed in a layer structure 20 is located. The layer structure 20 comprises for example three layers, a layer 23 of a material having piezoelectric properties being sputtered directly onto the first end 25, i.e. the end side of the screw head 2. The layer 23 is sputtered with a layer thickness of a few μm. A mechanical protection layer 22, the layer thickness of which is less than the layer thickness of the underlying layer 23 of a material having piezoelectric properties, is sputtered onto the layer 23. Lastly, the layer structure 20 according to the representation in FIG. 2.1 comprises at least one electrode layer 21. Individual electrodes are insulated from one another, as indicated by a spacing 26, inside the electrode layer 21 which constitutes a ring structure. In a first alternative embodiment, the layer structure represented in section in FIG. 2.1 may comprise an electrode layer of Sn, a mechanical protection layer 22 of CrO and a piezoelectric layer 23 having piezoelectric properties, which can be formed as a thin film with a layer thickness of a few μm. In another alternative embodiment of the ultrasound sensor 5 represented in section in the representation according to FIG. 2.1, the layer structure 20 may also—as in the first alternative embodiment—comprise an electrode layer 21 of titanium while the mechanical protection layer 22 is made of SiN, silicon nitride, and the piezoelectric layer 23 having piezoelectric properties is formed as a ZnO layer. Instead of a three-layered structure, however, the layer structure 20 may also have merely two layers if the mechanical protection layer 22 is omitted and the layer structure 20 merely comprises the electrode layer 21 and the piezoelectric layer 23 made of a material having piezoelectric properties.

The ultrasound sensor 5 represented in FIG. 2.1, formed as a layer structure 20, may also be sputtered on a second end 27 of the connection component 1 which is likewise freely accessible.

That which is represented in FIG. 2.1 by way of example, with reference to the example of a connection component 1 formed as a screw, may also be carried out on a connection component 1 which is configured as a bolt, a rivet or a pin.

The ultrasound sensor 5 with the layer structure 20, proposed according to the invention and integrated in the connection component 1, is distinguished by very high adhesion for example on the first end 25, formed as an end side, of the connection component 1. Owing to the high adhesion force of 20 N/mm2 or more, all coupling errors which could compromise the signal propagation time between the ultrasound sensor 5 and the connection component 1 are eliminated. It is therefore possible to achieve a much more accurate signal time of flight measurement and therefore a substantially more accurate determination of the prestress force or the stress force of the connection component 1. The connection component 1 may be made of the group of materials listed below: high-alloy steels, special steels, titanium and its alloys, in particular TiAl6V4, and aluminium and its alloys, and furthermore brass, Inconel (nickel alloy) and steels, for example A268, which are nonmagnetic, as well as all materials which can transmit ultrasound with a sufficient strength and in which evaluable echo structures are formed.

If the connection component 1 is made of a nonconductive material, for example plastic or a ceramic, then such a connection component 1 is first to be provided with a metallization layer in an additional first coating step, in order to produce the component mass.

Since each layer 21, 22, 23 inside the layer structure 20, i.e. the at least one electrode layer 21, the at least one mechanical protection layer 22 and the at least one piezoelectric layer 23, is applied by means of sputtering technology, high adhesion forces respectively prevail between the individual layers 21, 22, 23 of the layer structure 20. This applies not only for the contact side of the layer 23 of a material having piezoelectric properties and the first end 25 of the connection component 1, but also between the layers 21, 22, 23. Insulation of individual electrodes inside the electrode layer 21 can be carried out by the laser technique, in which case a laser beam, as will be described in more detail below, may be guided in a first possible embodiment in concentric circles over the first end 25, for example the end side of a screw head 2, or alternatively along a spiral track.

The thickness of the layer 23 of the material having piezoelectric properties can be more than the thickness of the mechanical protection layer 22 by a multiple.

For the electrode layer 21, into which the electrode structure formed for example in a ring shape is lasered by means of the laser method, the following materials may be selected: in a first possible embodiment, metals with or without nitrogen, for example titanium and TiN or the like, and chromium and CrN, or in another embodiment metal alloys, for example NiCr. When choosing the material from which the electrode layer 21 of the layer structure 20 of the ultrasound sensor 5 is made, it is preferable to use elements of groups IV, IVb, VIb, VIIIb, Ib, i.e. for example Sn, Ag, Ti or other compounds or metals with one another, for example NiCr, as well as other electrode-compatible materials.

The representation according to FIG. 2.2 shows a two-layered layer structure of an ultrasound sensor.

When using suitable thermally stable and environmentally resistant materials for the piezo layer, the protective layer may be obviated. In this case, the ultrasound sensor 5 is in the form of a two-layered structure 20 having an electrode layer 21 and precisely this layer 23 having piezoelectric properties, made of thermally stable and environmentally resistant piezo material.

Figure 3:
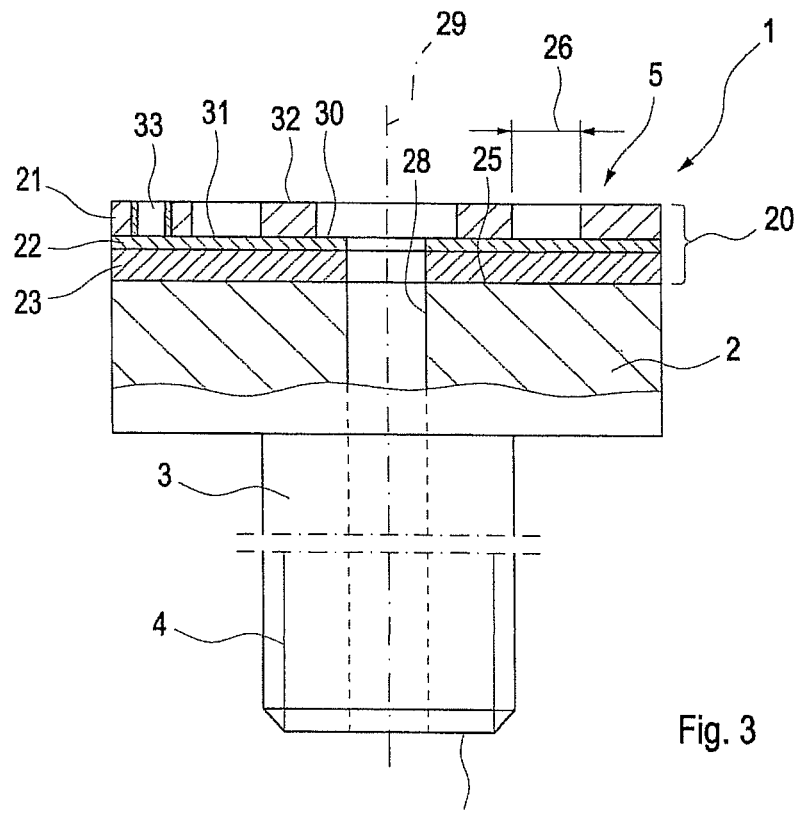
FIG. 3 shows the representation of a connection component comprising a through-bore and an ultrasound sensor with a ring geometry applied on the end side.

FIG. 3 shows a connection component having a through-bore, the ultrasound sensor being arranged on one of the end sides of the connection component.

FIG. 3 shows that the connection component 1 comprises a shank 3, which merges into a screw thread 4, below the screw head 2. The ultrasound sensor 5 is arranged on a first end side 25 of the connection component 1. The other, second end side of the connection component 1 according to the representation in FIG. 3 is identified by reference 27. The through-bore 28 is formed symmetrically with respect to the axis 29. On the first end side 25 of the connection component 1, formed in this case as a screw, there is the layer structure 20 of the ultrasound sensor 5, comprising an electrode layer 21, a mechanical protection layer 22 and a piezoelectric layer 23. FIG. 3 shows that a first laser-ablated region 30 is produced on the first end side 25 of the connection component 1 around the through-bore 28, and is surrounded by a second laser-ablated region 31 concentrically enclosing it. A metal ring electrode 32 remains between the laser-ablated regions 30, 31.

Figure 4:
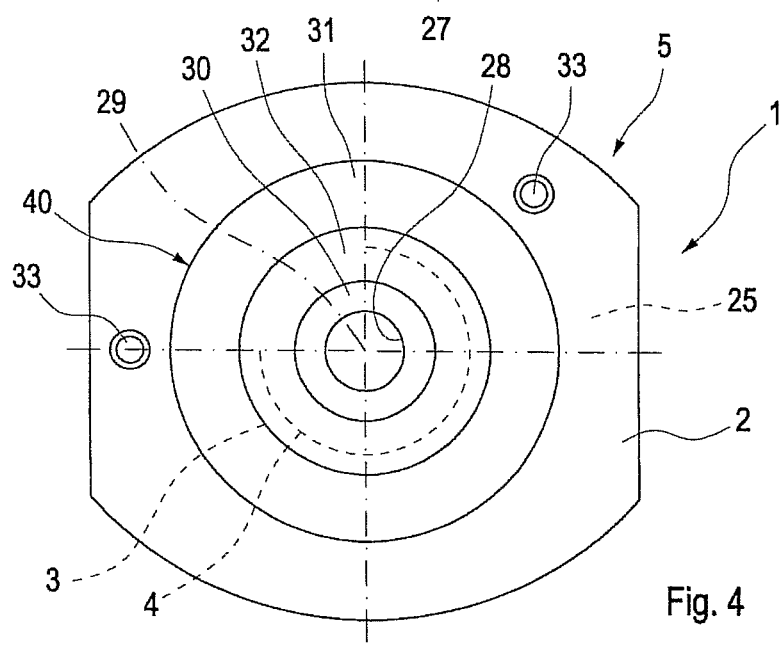
FIG. 4 shows the plan view of the end side of the connection component according to FIG. 3, FIGS. 5.1 and 5.2 show a plan view and side view of a connection component comprising a composite sensor formed by a plurality of individual sensors.

The second laser-ablated region 31 can be seen in the plan view according to FIG. 4. During the laser ablation, the first laser-ablated region 30 and the second laser-ablated region 31 are produced over a section of the connection component 1.

The laser ablation of the surfaces, which are closed on themselves, can be carried out in one working step by means of a continuous laser trace without jumps of the laser beam, so that damage to the piezoelectric layer 23 and the protective layer 22 optionally covering it can be avoided when laser-ablating the regions 30, 31. If a further electrode structure is laser-ablated as a reference element, then this is formed in particular on a part of the connection component 1 which is not stressed by mechanical stresses, i.e. on the first end side 25 of the connection component 1 which does not experience forces. By means of this further electrode structure, a temperature measurement can advantageously be carried out by means of ultrasound. By producing this further electrode structure on the first end side 25 of the connection component 1—in this case made in the form of a screw—decoupling of the temperature measurement from the axial force measurement is achieved.

FIG. 4 shows that there are reference elements 33 in the connection component 1 represented therein, which can be used for the temperature measurement by means of ultrasound, on the screw head 2.

The representations according to FIGS. 5.1 and 5.2 show another possible embodiment of an ultrasound sensor, which is configured as a composite sensor comprising a plurality of individual sensors.

As can be seen from the plan view according to FIG. 5.1 of the second end side 27 of the connection component 1, there are a plurality of individual sensors 34 on the second end side 27. The individual sensors 34, of which there are four in this case, together form a composite sensor 38. The individual sensors 34 are respectively connected to one another by electrical couplings 35. It can be seen from the plan view according to FIG. 5.1 that the individual sensors 34 are arranged at an angle 36 with respect to the horizontal. The distribution angle 36, or the arrangement of the individual sensors 34, is selected so that they are always arranged in the region in which, lying in the plane of the drawing, there is still sufficient material. This is the case particularly in the regions which are not penetrated by a first transverse bore 39 or a second transverse bore 57, intersecting with the first. As shown by FIG. 5.1, the individual sensors 34 of the composite sensor 38 are arranged in particular at an angle of about 45° with respect to the horizontal, so that all the individual sensors 34 always lie between the individual sections of the transverse bores 39, 57. This can be seen in particular from the representation according to FIG. 5.2, in which the first transverse bore 39 lies in the plane of the drawing while the second transverse bore 57, extending at a right angle to it, lies at an angle of 90° thereto. The individual sensors 34 located on the second end side 27 are arranged in such a way that they always lie over a material web 58 of the connection component 1 so that—as already represented in FIG. 1—a reliable sound path 6 is formed.

Figure 6:
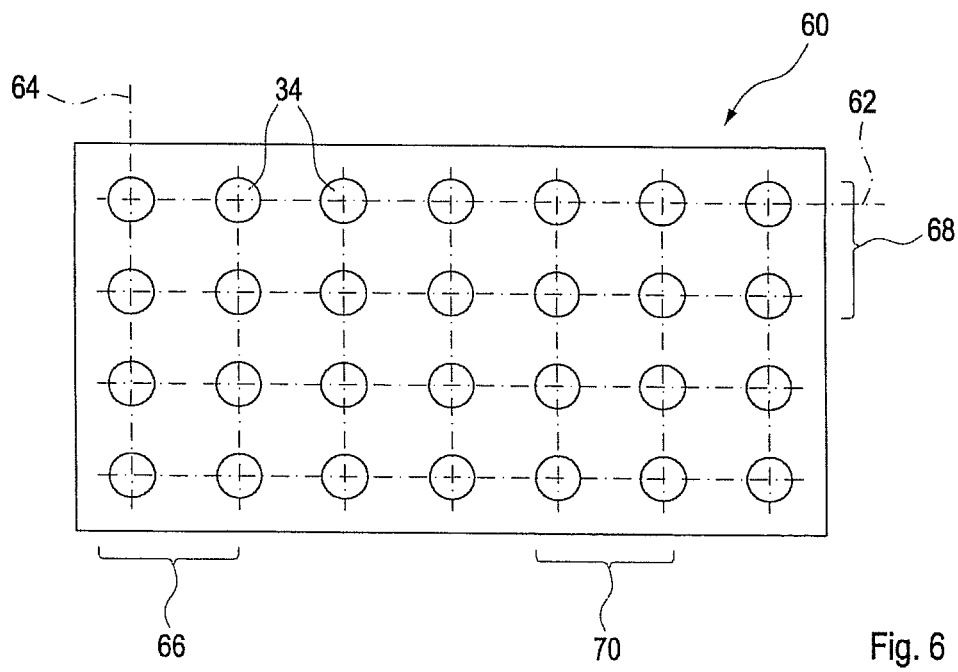
FIG. 6 shows a sensor array arranged in a matrix fashion.

As an alternative to the representation according to FIGS. 5.1 and 5.2, in which a composite sensor comprises a plurality of individual sensors, the representation according to FIG. 6 shows an ultrasound sensor array. A sensor array 60 comprises a plurality of individual sensors 34. They are arranged along a first axis 62, or along a second axis 64, on a support substrate. In this alternative embodiment, for example, individual sets 66, 68, 70 of a plurality of individual sensors 34 lying either on one axis 62 or on both axes 62, 64, can be driven and powered separately so that ultrasound signal measurements can be carried out at arbitrary positions by the sensor array 60 according to the representation in FIG. 6.

The individual sensors 34 can be driven independently of one another, so that an ultrasound measurement can be carried out at arbitrary positions of a workpiece. They may, however, also be interconnected in any desired groups.

Figures 7, 8:
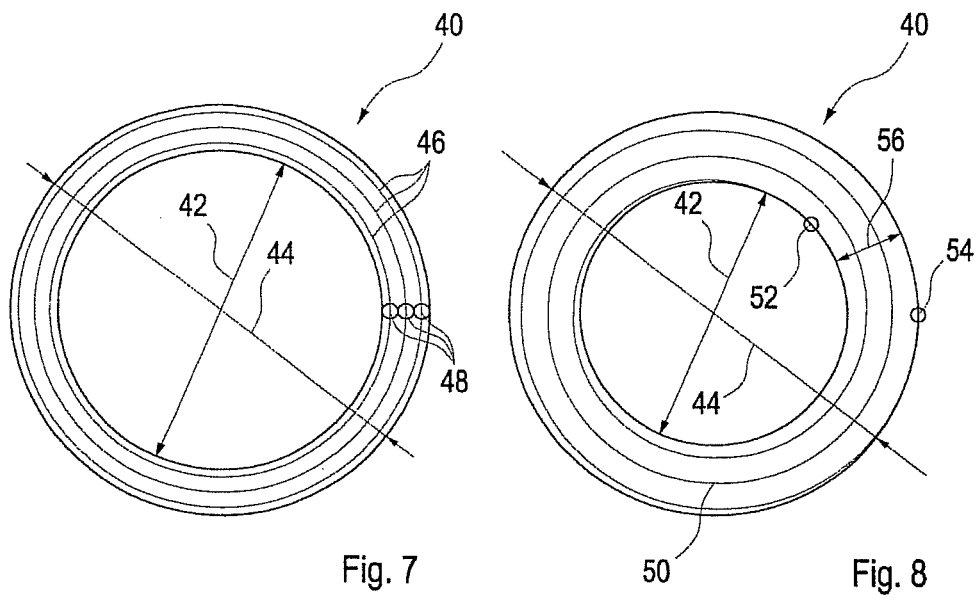
FIGS. 7 and 8 show a comparison of the lasering of a ring structure for producing a circularly round electrode by means of concentric circles and a spiral track of the laser beam, respectively.

The representation according to FIGS. 7 and 8 shows that a ring structure 40 for separating a first electrode 60 from a second electrode 62 on a first end 25 of the connection component 1 can be produced both by a plurality of concentrically extending tracks 46 of the laser beam and by a single spiral track 50 of the laser beam. The representation according to FIGS. 7 and 8 shows that in the case of concentric tracks 46, a number of insertion points 48 are produced where the laser beam both enters and emerges again. This entails the disadvantage that in the case of concentric tracks 46, their start and their end are respectively engaged by the laser beam, whence increased material erosion there which may extend into the mechanical protection layer 22. The material erosions on the mechanical protection layer 22 are tolerable, but it is necessary to avoid exposing or damaging the piezoelectric thin film 23 owing to an excessive penetration depth of the laser beams of the laser head.

Whereas the concentric track 46 of the laser beam as represented in FIGS. 7 and 8 leads to tracks separated discretely from one another inside the ring structure 40, a continuous uninterrupted track is obtained with a laser beam processing path extending in a spiral shape 50. This means that, as shown by the representation according to FIG. 5, a ring structure 40 is produced with a ring width 56 which comprises precisely one entry point 52 and precisely one exit point 54. This is important in particular since the concentric guiding 46 or the guiding of the laser beam carried out in the shape of a spiral, as represented in FIGS. 7 and 8, avoids a locally excessive energy input and therefore damage to the protective layer 22 or even the underlying piezo layer 23, so that the solution proposed according to the invention provides a method for the semiautomatic or fully automatic manufacture of ultrasound sensors in mass production. Laser ablation of ring structures by means of a spiral track 50 of the laser beam is to be preferred over laser ablation of ring structures in concentric circles.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

The invention claimed is:

1. A method for producing a connection component, the method comprising:
providing a connection component having an integrated ultrasound sensor, the integrated ultrasound sensor configured to analyze a mechanical stress distribution or configured to determine a prestress force of the connection component, and the ultrasound sensor having an at least two-layered layer structure comprising an electrode layer and, at least one layer of a material having piezoelectric properties, wherein the electrode layer and the layer of a material having piezoelectric properties are vapor deposited or sputtered on at least one freely accessible end of the connection component; and
laser-ablating structures for at least one, electrode of an arbitrary shape on a least one end side of the connection component,
wherein laser ablation of the structures, in order to form the electrodes with an arbitrary shape, is carried out so that after erosion of a metal layer an underlying layer of a material having piezoelectric properties or the protective layer is damaged minimally or not at all by an intensity of the laser radiation.

2. The method according to claim 1, wherein the layers of the at least two-layered layer structure have a sufficient adhesion force.

3. The method according to claim 1, further comprising applying the layer of a material having piezoelectric properties with a sufficient adhesion force onto a first end and/or a second end of the connection component.

4. The method according to claim 1, wherein the at least two-layered layer structure comprises at least one electrode layer, a mechanical protection layer, and at least one layer of a material having piezoelectric properties.

5. The method according to claim 4, further comprising forming the at least one layer of a material having piezoelectric properties to be thicker than the mechanical protection layer.

6. The method according to claim 1, further comprising applying the integrated ultrasound sensor on a freely accessible first end of the connection component onto a surface which is concave, convex, planar or corrugated, or surfaces formed from combinations thereof.

7. The method according to claim 1, wherein the structure comprises at least one concentrically laser-ablated circle.

8. The method according to claim 1, further comprising laser-ablating the structure in the form of a continuous uninterrupted track.

9. The method according to claim 8, wherein the track has at least one entry point and at least one exit point of a laser beam.

10. The method according to claim 1, further comprising arranging a composite sensor comprising one or more individual sensors on at least one end side.

11. The method according to claim 10, further comprising electrically coupling the individual sensors of the composite sensor to one another.

12. The method according to claim 10, further comprising arranging the individual sensors of the composite sensor on at least one end side of the connection component with a distribution angle such that the individual sensors lie over material webs of the connection component, which offer an optimal sound path for the ultrasound signals.

13. The method according to claim 1, further comprising arranging individual sensors as an ultrasound sensor array, so as to be oriented along a first axis and/or a second axis, and drivable in arbitrary sets.

14. The method according to claim 1, further comprising producing at least two laser-ablated regions in order to form the structures of at least one electrode with an arbitrary structure by the laser beam, in each case continuously in one working step.

15. The method according to claim 1, wherein the connection component is one of a screw, a connection bolt, a rivet and a pin.

16. A method for producing a connection component the method comprising;
providing a connection component having an integrated ultrasound sensor, the integrated ultrasound sensor configured to analyze a mechanical stress distribution or configured to determine a prestress force of the connection component, and the ultrasound sensor having an at least two-layered layer structure comprising electrode layer and at least one layer of a material having piezoelectric properties, wherein the electrode layer and the layer of a material having piezoelectric properties are vapor deposited or sputtered on at least one freely accessible end of the connection component; and laser-ablating structures for at least one electrode of an arbitrary shape on at least one end side of the connection component, wherein the wavelength of the laser radiation and other laser parameters, including a pulse frequency, are adapted to an absorption capacity of the layers of the at least two-layered layer structure of the ultrasound sensor.

17. A method for producing a connection component, the method comprising:

providing a connection component having an integrated ultrasound sensor, the integrated ultrasound sensor configured to analyze a mechanical stress distribution or configured to determine a prestress force of the connection component, and the ultrasound sensor having an at least two-layered layer structure comprising an electrode layer and at least one layer of a material having piezoelectric properties, wherein the electrode layer and the layer of a material having piezoelectric properties are vapor deposited or sputtered on at least one freely accessible end of the connection component; and laser-ablating structures for at least one electrode of an arbitrary shape on at least one end side of the connection component, wherein a further laser-ablated structure, via which a temperature measurement is carried out via ultrasound, is produced on at least one end side of the connection component outside a region stressed by mechanical stresses.

18. A method for producing a connection component, the method comprising:

providing a connection component having an integrated ultrasound sensor, the integrated ultrasound sensor configured to analyze a mechanical stress distribution or configured to determine a prestress force of the connection component, and the ultrasound sensor having an at least two-layer structure comprising an electrode layer and at least one layer of a material having piezoelectric properties, wherein the electrode layer and the layer of a material having piezoelectric properties are vapor deposited or sputtered on at least one freely accessible end of the connection component; and laser-ablating structures for at least one electrode of an arbitrary shape on at least one end side of the connection component, wherein the individual sensors of a sensor array are driven independently of one another in freely definable sets along a first axis and/or a second axis.

* * * * *